United States Patent [19]

Schmerling

[11] 4,036,896

[45] July 19, 1977

[54] PRODUCTION OF CHLORO-SUBSTITUTED SATURATED COMPOUNDS

[75] Inventor: Louis Schmerling, Riverside, Ill.

[73] Assignee: Universal Oil Products Company, Des Plaines, Ill.

[21] Appl. No.: 574,988

[22] Filed: May 6, 1975

[51] Int. Cl.² ............................................. C07C 17/00
[52] U.S. Cl. .............................. 260/648 R; 260/648 C; 260/651 R; 260/658 R
[58] Field of Search ........... 260/648 R, 648 C, 651 R, 260/658 R

[56] References Cited

U.S. PATENT DOCUMENTS

| 2,502,369 | 7/1951 | Schmerling | 260/648 R |
|---|---|---|---|
| 2,914,572 | 11/1959 | Amir | 260/648 R |

FOREIGN PATENT DOCUMENTS

| 161,712 | 4/1964 | U.S.S.R. | 260/648 R |
|---|---|---|---|

*Primary Examiner*—C. Davis
*Attorney, Agent, or Firm*—James R. Hoatson, Jr.; Raymond H. Nelson; William H. Page, II

[57] ABSTRACT

Chloro-substituted saturated compounds are prepared by condensing a saturated hydrocarbon containing at least 3 carbon atoms and a hydrogen atom attached to a secondary or tertiary carbon atom or to a carbon atom which is attached to an aromatic ring with a chloromonoolefin in which the chlorine is attached to a carbon atom other than a doubly-bonded carbon atom in the presence of a free-radical generating catalyst, preferably in the presence of a promoter comprising a hydrogen chloride compound.

14 Claims, No Drawings

PRODUCTION OF CHLORO-SUBSTITUTED SATURATED COMPOUNDS

This invention relates to a process for the production of chloro-substituted saturated compounds. More specifically, this invention relates to a process for the preparation of chloro-substituted saturated compounds which comprises condensing a saturated hydrocarbon containing at least 3 carbon atoms and a hydrogen atom attached to a secondary or tertiary carbon atom or to a carbon atom attached to an aromatic ring with a chloromonoolefin in which a chlorine atom is attached to a carbon atom other than one of the doubly-bonded carbon atoms in the presence of a free radical-generating catalyst and preferably in the presence of a promoter comprising a hydrogen chloride compound.

The free radical-induced reaction of a saturated hydrocarbon with an unsaturated hydrocarbon is well known in the prior art. It is also known in the art that a saturated hydrocarbon may be condensed by means of free radical-generators with a chloroolefin characterized by the presence of at least one chlorine atom on each of the doubly-bonded carbon atoms. Further, it has been subsequently shown that the condensation may be performed in the presence of the free radical-generators with a chloroolefin characterized by the presence of only one chlorine atom attached to either of the doubly-bonded carbon atoms.

In contradistinction to the prior art it has now been discovered that a saturated hydrocarbon containing at least 3 carbon atoms and a hydrogen atom attached to a secondary or tertiary carbon atom or to a carbon atom which is attached to an aromatic ring may also be condensed with a chloromonoolefin in which a chlorine atom is attached to a carbon atom other than a doubly-bonded carbon atom. The condensation may be induced by the presence of a free radical-generating compound such as a peroxy compound and the reaction may optionally be enhanced by the presence of a promoter comprising a hydrogen chloride compound. The utilization of the above set forth hydrogen chloride compound will produce a greater percentage conversion of the original reactants, namely, the saturated hydrocarbon and the chloromonoolefin, and an increased percent yield of the chloro-substituted saturated compound.

The desired products of the present invention, chloro-substituted saturated compounds, are utilized in the chemical industry in many ways. For example, the heavier molecular weight chloro-substituted saturated compounds may be converted to alcohols for the further use in the preparation of detergents. Likewise, allyl-substituted cyclohexane produced by the process of the present invention may be utilized in the preparation of (2-hydroxypropyl)cyclohexane by hydration, to (2-acyloxypropyl)cyclohexane by esterification of an acid, and to other derivatives; as a thermosetting resin for varnishes, plastics, adhesives; or in the synthesis of pharmaceuticals and insecticides; etc.

It is therefore an object of this invention to provide a process for the preparation of chloro-substituted saturated compounds.

A further object of this invention is to provide a process for the preparation of chloro-substituted saturated compounds utilizing a certain promoter composition of matter comprising a hydrogen chloride compound which will permit a more economically desirable batch and continuous type process.

In one aspect an embodiment of this invention resides in a process for producing a chloro-substituted saturated compound which comprises condensing a saturated hydrocarbon containing at least 3 carbon atoms and a hydrogen atom atached to a secondary or tertiary carbon atom or to a carbon atom which is attached to an aromatic ring hydrocarbon with a chloromonoolefin in which the chlorine is attached to a carbon atom other than a doubly-bonded carbon atom in the presence of a free radical-generating catalyst at reaction conditions, and recovering the resultant chloro-substituted saturated compound.

In another aspect an embodiment of this invention resides in a process for the preparation of a chloro-substituted saturated compound which comprises condensing a saturated hydrocarbon containing at least three carbon atoms and a hydrogen atom attached to a secondary or tertiary carbon atom or to a carbon atom which is attached to an aromatic ring with a chloromonoolefin in which a chlorine atom is attached to a carbon atom other than a doubly-bonded carbon atom in the presence of a free radical-generating catalyst and a promoter comprising a hydrogen chloride compound at reaction condition and recovering the resultant chloro-substituted saturated compound.

A specific embodiment of this invention resides in a process for preparing allylcyclohexane and chloropropylcyclohexanes which comprises condensing cyclohexane with allyl chloride at a temperature in the range of 130° to about 140° C. in the presence of a catalyst comprising di-t-butyl peroxide and recovering the resultant allylcyclohexane, (2-chloropropyl)cyclohexane) (i.e., 2-chloro-1-cyclohexylpropane), and (3-chloropropyl)cyclohexane (i.e. 1-chloro-3-cyclohexylpropane).

Another specific embodiment of this invention resides in a process for preparing allylcyclohexane which comprises condensing cyclohexane with allyl chloride at a temperature of 130° to 140° C. and a pressure of 1 atmosphere in the presence of a catalyst comprising di-t-butyl peroxide and a promoter comprising aqueous concentrated hydrochloric acid and recovering the resultant allylcyclohexane together with 2-chloro-1-cyclohexylpropane and 1-chloro-3cyclohexylpropane.

Yet another specific embodiment of this invention resides in a process for preparing 1-chloro-4,4dimethylhexane which comprises condensing isopentane with allyl chloride at a temperature of about 130° to 140° C. and a pressure of 1 atmosphere in the presence of a catalyst comprising di-t-butyl peroxide and a promoter comprising anhydrous hydrogen chloride, and recovering the resultant 1-chloro-4,4-dimethylhexane.

Other objects and embodiments of the present invention will be found in the following further detailed description of the present invention.

As hereinbefore set forth, the present invention is concerned with a process for preparing chloro-substituted saturated compounds which comprises condensing a saturated hydrocarbon containing at least 3 carbon atoms and a hydrogen atom attached to a secondary or tertiary carbon atom or to a carbon atom attached to an aromatic ring with a chloromonoolefin in which the chlorine atom is attached to a carbon atom other than one of the doubly-bonded carbon atoms in the presence of a free radical-generating catalyst and optionally in the presence of a promoter comprising a hydrogen chloride compound.

The reaction is effected under conditions which include an elevated temperature of at least as high as the initial decomposition temperature of the free radical-generating catalyst. In addition, another reaction condition involves pressure, said pressure ranging from about atmospheric to about 100 atmospheres or more. When superatmospheric pressures are employed, said pressures are afforded by the introduction of vaporized reactants or a substantially inert gas such as nitrogen into the reaction zone. Another variable which is employed is the amount of reactants, the saturated hydrocarbon containing at least 3 carbon atoms and a hydrogen atom attached to a secondary or tertiary carbon atom or to a carbon atom attached to an aromatic ring usually being present in a mol ratio in the range of from about 1:1 up to about 10:1 mols of the saturated hydrocarbon per mol of chloromonoolefin in which the chlorine atom is attached to a carbon atom other than either the carbon atoms which are doubly-bonded to one another.

Examples of suitable saturated hydrocarbons containing at least 3 carbon atoms and a hydrogen atom attached to a secondary or tertiary atom or to a carbon attached to an aromatic ring which are utilized as one of the starting materials in the process of this invention, include non-cyclic alkanes containing at least 3 carbon atoms up to about 20 carbom atoms and cycloalkanes possessing from about 5 to about 8 carbon atoms. Suitable examples of saturated hydrocarbons include propane, n-butane, n-pentane, tetradecanes, isobutane, isopentane, methylpentanes, methylhexanes, methylheptanes, methyloctanes, methylnonanes, 2,2,4-trimethylpentane, isooctane, 2,2,5-trimethylpentane, 2,4-dimethylhexane, 2,3-dimethylheptane, 4-ethyloctane, 5-propylnonane, 2,3-dimethyldecane, 4,5-dipropyldecane, 2,3-dimethylundecane, 3,4-diethyltridecane, neohexanes, neoheptanes, cyclopentane, methylcyclopentane, cyclohexane, methylcyclohexane, cycloheptane, cyclooctane, bicyclopentyl, bicyclohexyl, bicycloheptyl, bicyclooctyl, decahydronaphthalene, etc. For the purposes of this invention alkylbenzenes and cycloalkylbenzenes (and other alkylated aromatic hydrocarbons) containing at least 1 hydrogen atom attached to a carbon atom which is attached to the aromatic ring are considered to be saturated hydrocarbons. These include toluene, ethylbenzene, n-, and isobutylbenzene and similar compounds containing up to 10 carbon atoms in the alkyl group such as n- and isodecylbenzene.

Suitable chloromonoolefins which may be condensed with the aforementioned saturated hydrocarbon containing at least 3 carbon atoms and a hydrogen atom attached to a secondary or tertiary carbon atom will include chloromonoolefins in which a chlorine atom is attached to a carbon atom which is not one of the doubly-bonded carbon atoms, including the non-cyclic and cyclic monoolefins. Such chloromonoolefins will include allyl chloride, crotyl chloride, 2-methylallyl chloride, ethylallyl chlorides, propylallyl chlorides, butylallyl chlorides, pentylallyl chlorides, hexylallyl chlorides, heptylallyl chlorides, octylallyl chlorides, nonylallyl chlorides, decylallyl chlorides, dodecylallyl chlorides, tetradecylallyl chlorides, pentadecaalyl chlorides, hexadecylallyl chlorides, nonadecylallyl chlorides, 3-chloro-1-butene, 3,4-dichloro-1-butene, 4-chloro-1-pentene, 4,5-dichloro-1-pentene, 5-chloro-1heptene, 3,5-dichloro-1heptene, 4,5-dichloro-1-heptene, 6-chloro-1-octene, 5-chloro-1-nonene, 5,6-dichloro-2-nonene, 6,7,8-trichloro-3-decene, 3,4,5,6-tetrachloro-1-undecene, 4,5,6,7-tetrachloro-1-dodecene, 7-chloro-1-tetradecene, 12-chloro-1-tetradecene, 3,4,5,6,7-pentachloro-2-pentadecene, 6-chloro-2-nonadecene, 3-chloro-1-cyclohexene, 4-chloro-1-cyclohexene, 5-chloro-1-cyclohexene, 3,4-dichloro-1-cyclohexene, 3,4,5-trichloro-1-cyclohexene, etc.

The catalytic composition of matter which are to be used in the process of the present invention comprise organic peroxides which are designated as free radical-generating catalysts. Examples of these catalysts which may be used include, in particular, the di-substituted hydrogen peroxides such as di-t-butyl peroxide, t-butyl perbenzoate, benzoyl peroxide, etc. It is also contemplated within the scope of this invention that hydroperoxides such as acetyl hydroperoxide and t-butyl hydroperoxide may also be used although not necessarily with equivalent results.

The particular catalytic composition of matter chosen in the process of the present invention has an effect upon the reaction temperature in that the reaction temperature should be at least as high as the initial decomposition temperatures of the free radical-generating catalyst such as the peroxide compound, in order to liberate and form free radicals which promote the reaction. In selecting the particular reaction temperature for use in the process of the present invention two considerations must be taken into account. First, sufficient energy by means of heat must be supplied to the reaction system so that reactants, namely, the saturated hydrocarbon containing at least 3 carbon atoms and a hydrogen atom attached to a secondary or tertiary carbon or to a carbon atom which is attached to an aromatic ring and the chloromonoolefin in which the chlorine atom is attached to a carbon atom other than one of the doubly-bonded carbon atoms, will be activated sufficiently for condensation to take place when free radicals are generated by the catalyst. Second, free radical-generating catalyst such as the peroxy compounds, particularly organic peroxides, decompose at a measurable rate with time in a logarithmic function dependent upon temperature. The rate of decomposition can be, and ordinarily is, expressed as the half-life of the peroxide at a particular temperature. For example, the half-life in hours at di-t-butyl peroxide is 17.5 hours at 125° C., 5.3 hours at 135° C. and 1.7 hours at 145° C. (calculated from data for the first 33% decomposition). A reaction system temperature can be selected so that the free radical-generating catalyst decomposes smoothly with the generation of free radicals at the half-life which is not too long. In other words, sufficient free radicals must be present to induce the present chain reaction to take place, and these radicals must be formed at temperature at which the reactants are in a suitable activated state for condensation. When the half-life of the free radical-generating catalyst is greater than 10 hours, radicals are not generated at a sufficient rate to cause a reaction of the process of the present invention to go forward at a practical rate. Thus, the reaction temperature may be within the range of from about 50° to about 300° C. and at least as high as the decomposition temperature of the catalysts, by which is meant a temperature such that the half-life of the free radical-generating catalyst is not greater than 10 hours. Since the half-life for each free radical-generating catalyst is different at different temperatures, the exact temperature to be utilized in a particular reaction will vary. However, persons skilled in the art are well acquainted with the half-life versus the temperature data for different free radical-generating catalysts. Thus, it is within the skill of one familiar with the art to select a particular temperature needed for any particular catalyst. However, the operating temperature generally does not exceed the decomposition temperature of the catalyst by more than about 150° C. since free radical-generating catalysts decompose rapidly under such conditions. For example, when a free radical-generating catalyst such as t-butyl perbenzoate is used having a decomposition temperature of approximately 115° C., the process is run at a temperature ranging from about 115° to about 265° C. When di-t-butyl peroxide having a decomposition temperature of about 130° C. is used, the process is run at a temperature ranging from about 130° to about 280° C. Higher reaction temperatures may be employed but little advantage is gained if the temperature is more than the hereinbefore mentioned 150° C. higher than the decomposition temperature of the catalyst. The general effect of increasing the operating temperature is to accelerate the rate of condensation reaction between the chloromonoolefin in which the chlorine atom is attached to a carbon other than the doubly-bonded carbon atoms and the saturated hydrocarbon containing at least 3 carbon atoms and in which the hydrogen atom is attached to a secondary or tertiary carbon atom or to a carbon atom which is attached to an aromatic ring. However, the increased rate of reaction may be accompanied by a certain amount of undesirable side reactions such as polymerization of the chloromonoolefin. It is contemplated within the scope of this invention that a promoter comprising a hydrogen chloride compound will enhance the quantity of chloro-substituted saturated compounds produced in the process of this invention. The term "hydrogen chloride compound" is defined to mean either anhydrous hydrogen chloride or aqueous hydrogen chloride. The effect of the hydrogen chloride compound upon the mechanism of the hereinbefore set forth reaction is that of increasing the yield of the chloro-substituted products. The mechanism of the reaction of the hydrogen chloride (which exhibits a marked and unique effect upon the free radical induced alkyl atoms) is shown by the following mechanism:

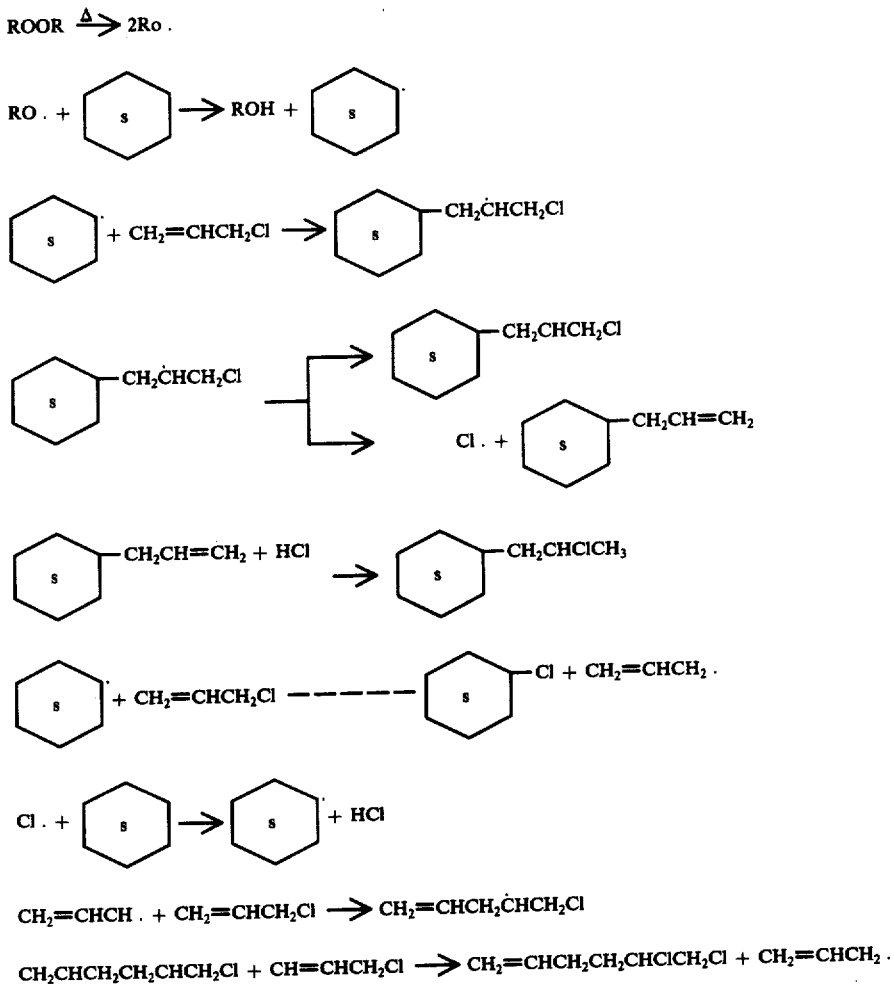

It is understood that the aforementioned saturated hydrocarbons containing at least 3 carbon atoms and a hydrogen atom attached to a secondary or tertiary carbon atom or to a carbon atom which is attached to an aromatic ring, chloromonoolefins in which the chlorine atom is attached to a carbon atom which is other than a doubly-bonded carbon atom, and free radical-generating catalysts are only representative of the class of compounds which may be employed and that the present invention is not necessarily limited thereto.

The process of this invention may be effected in any suitable manner and may comprise either a batch or a continuous type operation. For example when a batch type operation is employed the reactants comprising the saturated hydrocarbon containing at least 3 carbon atoms and a hydrogen atom attached to a secondary or tertiary carbon atom or to a carbon atom which is attached to an aromatic ring and the chloromonoolefin in which the chlorine atom is attached to a carbon atom other than a doubly-bonded carbon atom are placed in an appropriate apparatus along with a free radical-generating catalyst which may have a promoter comprising a hydrogen chloride compound added thereto. If atmosphere pressure is to be employed, the reaction vessel is then heated to a predetermined operating temperature. After maintaining the reactants in the reaction vessel at this temperature (suitably under reflux conditions particularly when high-boiling reactants and anhydrous hydrogen chlorides are used for a period of time which may range from 0.5 up to 30 hours or more in duration, the heating is discontinued and the reaction vessel allowed to return to room temperature. The reaction mixture is then recovered, separated from the catalyst and the promoter and subjected to conventional means of purification and separation, said means include washing, drying, extraction, evaporation, fractional distillation, etc. whereby the desired chloro-substituted saturated compound is recovered. Alternatively, if superatmospheric pressures are to be employed the reaction, the reactants are charged to a pressure vessel such as a rotating autoclave which contains a free radical-generating catalyst to which a promoter comprising a hydrogen chloride compound may have been added if it is desired in the condensation reaction. The autoclave is sealed and a substantially inert gas such as nitrogen or helium is pressed in until the desired pressure is reached. The autoclave is then heated to a desired operating temperature and maintained thereat for a predetermined residence time. At the end of this time heating is discontinued, the autoclave is allowed to return to room temperature and the excess pressure is discharged. The autoclave is opened and the reaction mixture is then treated in a manner similar to that hereinbefore set forth whereby the desired chloro-substituted saturated compounds are separated and recovered.

It is also contemplated within the scope of this invention that the reaction process for obtaining a chloro-substituted saturated compound may be effected in any continuous manner of operation. When such a type of process is employed, the reactants comprising the saturated hydrocarbon containing at least 3 carbon atoms and a hydrogen atom attached to a secondary or tertiary carbon atom or to a carbon which is attached to an aromatic ring and a chloromonoolefin in which the chlorine atom is attached to a carbon atom which is other than a doubly-bonded carbon atom are continuously charged to the reaction vessel under conditions of good mixing as are the free radical-generating catalysts and the promoters comprising the hydrogen chloride compound, if used; however, the reactants, the catalysts and the promoter may be added from the same or different inlet lines. After completion of the desired residence time, the reactor effluent is continuously withdrawn and subjected to conventional means of separation whereby the desired chloro-substituted saturated compounds are recovered while any unreacted starting material comprising the saturated hydrocarbon or the chloromonoolefin are recycled to the reaction zone to form a portion of the feedstock.

Examples of chloro-substituted saturated compounds which may be prepared according to the process of this invention will include monochloro-substituted saturated compounds and polychloro-substituted saturated compounds such as 1-chloro-4,4-dimethylhexane, 2-chloro-1-cyclohexylpropane, 1-chloro-3-cyclohexylpropane, dimers of allyl chloride such as 5,6-dichloro-1-hexene, dimers of methylallyl chloride, 5,6-dichloro-1-cyclohexylhexane, (3,4-dichlorobutyl)cyclohexane, (5-chlorooctyl)cyclohexane, etc. Hydrocarbon by-products which may be produced include allylcyclohexane, methallylcyclohexane, crotylcyclohexane, etc.

The following examples which are given to illustrate the process of the present invention are not, however, intended to limit the generally broad scope of the present invention in strict accordance therewith.

EXAMPLE I

In this example 39.0 grams of cyclohexane, 86.0 grams of allyl chloride and 6.0 grams of di-t-butyl peroxide were sealed in a glass-lined 850 ml rotating autoclave. The rotating autoclave was heated to a temperature of 130° to 140° C. at an initial pressure of 30 atmospheres of nitrogen pressure for a period of time comprising 4 hours. At the end of this time, heating was terminated and the autoclave vented, thereby allowing said autoclave to return to ambient pressure. The product was separated from the autoclave, distilled and analyzed by means of gas-liquid chromatography instrumentation, said analysis being set forth in mol percent yield in Table I below:

TABLE I

| PRODUCT | MOL PERCENT YIELD |
| --- | --- |
| allylcyclohexane | 13 |
| 5,6-dichloro-1-hexene | 12 |
| chlorocyclohexane | 5 |
| 2-chloro-1-cyclohexylpropane | 4 |
| (chlorohexenyl)cyclohexane | 3 |
| 1-chloro-3-cyclohexylpropane | 2 |

EXAMPLE II

In this example 83.0 grams of cyclohexane, 39.0 grams of allyl chloride, 6.0 grams of di-t-butyl peroxide and 22.0 grams of concentrated aqueous hydrochloric acid were added to a glass-lined 850 ml rotating autoclave. The autoclave was heated to a temperature of between 130° and 140° C. at an initial pressure of 30 atmospheres of nitrogen for a period of time comprising a period of 4 hours. At the end of this time, heating was terminated thereby allowing the autoclave to return to room temperature, and the autoclave was vented to relieve the excess pressure. The product was recovered from the autoclave, distilled and analyzed by gas-liquid chromatographic instrumentation. The analysis disclosed a yield in mol percent as set forth in Table II below:

TABLE II

| PRODUCT | MOL PERCENT YIELD |
| --- | --- |
| allylcyclohexane | 16 |
| 2-chloro-1-cyclohexylpropane | 14 |
| 5,6-dichloro-1-hexene | 12 |
| 1-chloro-3-cyclohexylpropane | 6 |
| (chlorohexenyl)cyclohexane | 3 |
| chlorocyclohexane | 2 |

A comparison of Table II with Table I of Example I demonstrates the effect of the hydrogen chloride promoter. The hydrogen chloride promoter was responsible for an increase in the mol percent yield of 2-chloro-1-cyclohexylpropane, and 1-chloro-3-cyclohexylpropane.

EXAMPLE III

In this example 84.0 grams of cyclohexane, 92.0 grams of methallyl chloride, 7.0 grams of t-butyl perbenzoate and 22.0 grams of anhydrous hydrogen chloride are added to an 850 ml rotating autoclave. Nitrogen is added to an initial pressure of 50 atmospheres and the rotating autoclave is maintained at a temperature of 115° C. for a period of time comprising 6 hours. At the end of the 6 hour period of time the heat to the rotating autoclave is terminated, thereby allowing it to return to room temperature, and the autoclave is subsequently vented to effect the egress of the nitrogen pressure gas. The product is recovered from the autoclave and analyzed by means of gas-liquid chromatography; said analysis will disclose the major condensation products to include 3-chloro-2-methyl-1-cyclohexylpropane, 2-chloro-2-methyl-1-cyclohexylpropane, and methallylcyclohexane.

EXAMPLE IV

In this example 100.0 grams of isopentane, 76.0 grams of allyl chloride, 6.0 grams of di-t-butyl peroxide and 35.0 grams of 37% aqueous hydrochloric acid are added to an 850 ml rotating autoclave. Nitrogen is charged to an initial pressure of 100 atmospheres for a period of time comprising 2 hours and the rotating autoclave is maintained at a temperature of 140° C. At the end of the 2 hour period of time the heat to the rotating autoclave is terminated, thereby allowing it to return to room temperature and the autoclave is subsequently vented. The product is recovered from the autoclave and analyzed by means of gas-liquid chromatography; said analysis will disclose the major condensation product to be 5,6-dichloro-1-hexene mixed with 1-chloro-4,4-dimethylhexane.

EXAMPLE VI

In this example 84.0 grams of cyclopentane, 40.0 grams of 3,4-dichloro-1-butene and 7.0 grams of t-butyl perbenzoate are added to an 850 ml rotating autoclave. The rotating autoclave is maintained at a temperature of 110°–115° C. and an initial nitrogen pressure of 30 atmospheres for a period of time comprising 6 hours. At the end of the 6 hours period of time the heat to the rotating autoclave is terminated, thereby allowing it to return to room temperature, and the autoclave is subsequently vented to remove excess nitrogen gas. The product is recovered from the autoclave and analyzed by means of gas-liquid chromatography, said analysis disclosing the major condensation products to be (3,4-dichlorobutyl)-cyclopentane, (2,4-dichlorobutyl)cyclopentane and (4-chlorocrotyl)cyclopentane.

I claim as my invention:

1. A process for producing a chloro-substituted saturated compound which comprises condensing a saturated hydrocarbon containing at least 3 carbon atoms and a hydrogen atom attached to a secondary or tertiary carbon atom or to a saturated side chain carbon atom which is attached to an aromatic ring hydrocarbon with a chloromonoolefin in which a chlorine atom is attached to a carbon atom other than one of the doubly-bonded carbon atoms in the presence of a free radical-generating catalyst at reaction conditions, and recovering the resultant chloro-substituted saturated compound.

2. The process of claim 1 further characterized in that the reaction conditions include a temperature at least as high as the decomposition temperature of the free radical catalyst and a pressure of from about 1 atmosphere to 100 atmospheres.

3. The process of claim 1 further characterized in that the free radical-generating catalyst is a peroxy compound.

4. The process of claim 3 further characterized in that the peroxy compound is di-t-butyl peroxide.

5. The process of claim 1 further characterized in that the reaction is effected in the presence of anhydrous or aqueous hydrogen chloride.

6. The process of claim 5 further characterized in that the hydrogen chloride is anhydrous hydrogen chloride.

7. The process of claim 5 further characterized in that the hydrogen chloride is aqueous hydrogen chloride.

8. The process of claim 1 further characterized in that the saturated hydrocarbon is an alkane possessing from about 3 carbon atoms to 20 carbon atoms.

9. The process of claim 1 further characterized in that the saturated hydrocarbon is a cycloalkane of from about 5 to about 8 carbon atoms.

10. The process of claim 1 further characterized in that the saturated hydrocarbon is an arylalkane in which the alkane chain possesses from about 3 to about 20 carbon atoms.

11. The process of claim 1 further characterized in that the saturated hydrocarbon is cyclohexane, the chloromonoolefin is allyl chloride and the chloro-substituted saturated compound comprises 1-chloro-3-cyclohexylpropane or 2-chloro-1-cyclohexylpropane.

12. The process of claim 1 further characterized in that the saturated hydrocarbon is cyclopentane, the chloromonoolefin is 3,4-dichloro-1-butene, and the chloro-substituted saturated compounds comprise (3,4-dichlorobutyl)cyclopentane, and (2,4-dichlorobutyl)cyclopentane.

13. The process of claim 1 further characterized in that the saturated hydrocarbon is cyclohexane, the chloromonoolefin is methallyl chloride and a chloro-substituted saturated compound comprises a chloro(cyclohexyl)methylpropane.

14. The process of claim 1 further characterized in that the saturated hydrocarbon is isopentane, the chloromonoolefin is allyl chloride and the chloro-substituted saturated compound comprises 1-chloro-4,4-dimethylhexane.

* * * * *